(12) United States Patent
Ferragamo et al.

(10) Patent No.: US 9,060,768 B2
(45) Date of Patent: Jun. 23, 2015

(54) TISSUE FIXATOR

(75) Inventors: Michael Charles Ferragamo, Foster, RI (US); Jeffrey Wyman, Naples, FL (US); Alfred Rodrique Berune, Jr., North Attleboro, MA (US); Michael James Perriello, Hopedale, MA (US); Gary Robert McCarthy, East Bridgewater, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/249,449

(22) Filed: Sep. 30, 2011

(65) Prior Publication Data

US 2012/0083837 A1 Apr. 5, 2012

Related U.S. Application Data

(60) Provisional application No. 61/388,056, filed on Sep. 30, 2010.

(51) Int. Cl.
*A61B 17/06* (2006.01)
*A61B 17/04* (2006.01)
*A61F 2/08* (2006.01)

(52) U.S. Cl.
CPC ......... *A61B 17/06004* (2013.01); *A61F 2/0811* (2013.01); *A61F 2002/0852* (2013.01); *A61B 17/0401* (2013.01); *A61B 2017/0404* (2013.01); *A61B 2017/0417* (2013.01);
(Continued)

(58) Field of Classification Search
CPC .......... A61B 17/06004; A61B 2017/0404; A61B 2017/06009; A61B 2017/06014; A61B 2017/06019; A61B 2017/06023; A61B 2017/06028; A61B 17/0487; A61B 17/0401; A61B 2017/0417; A61B 2017/061; A61B 2017/0608; A61F 2/08; A61F 2/0811; A61F 2002/0852
USPC .................................................. 606/222–227
See application file for complete search history.

(56) References Cited

U.S. PATENT DOCUMENTS

| 1,055,058 | A | * | 3/1913 | Leighton | 223/102 |
| 1,449,068 | A | * | 3/1923 | Snyder | 606/225 |
| 4,957,502 | A | * | 9/1990 | Takase | 606/223 |

(Continued)

FOREIGN PATENT DOCUMENTS

| DE | 252409 C | 11/1911 |
| DE | 835977 C | 4/1952 |

(Continued)

OTHER PUBLICATIONS

International Search Report and Written Opinion for PCT/US2011/054133 mailed Dec. 2, 2011.

(Continued)

*Primary Examiner* — Julian W Woo
*Assistant Examiner* — Shaun L David
(74) *Attorney, Agent, or Firm* — Chapin IP Law, LLC

(57) ABSTRACT

The present disclosure relates to a needle for attaching a fixator to a soft tissue graft. The needle includes a pointed distal end and a proximal end, the proximal end including a suture coupler, the suture coupler including a hook and a pocket formed by the hook, wherein the needle is curved along an entire length of the needle. A fixator for use with the needle and method of fixating a soft tissue graft to a bone is also disclosed.

8 Claims, 7 Drawing Sheets

(52) U.S. Cl.
CPC ............... *A61B 2017/06019* (2013.01); *A61B 2017/0608* (2013.01); *A61B 2017/061* (2013.01)

(56) References Cited

U.S. PATENT DOCUMENTS

| | | | | |
|---|---|---|---|---|
| 5,219,359 | A | * | 6/1993 | McQuilkin et al. ............ 606/232 |
| 5,306,301 | A | * | 4/1994 | Graf et al. ...................... 606/232 |
| 5,456,246 | A | | 10/1995 | Schmieding et al. |
| 5,593,424 | A | * | 1/1997 | Northrup, III ................. 606/232 |
| 5,643,295 | A | * | 7/1997 | Yoon ............................. 606/151 |
| 5,645,588 | A | | 7/1997 | Graf et al. |
| 5,913,875 | A | * | 6/1999 | Smith et al. .................... 606/222 |
| 6,533,802 | B2 | * | 3/2003 | Bojarski et al. ................ 606/232 |
| 7,530,990 | B2 | | 5/2009 | Perriello et al. |
| 2007/0233241 | A1 | * | 10/2007 | Graf et al. .................. 623/13.14 |
| 2008/0195148 | A1 | | 8/2008 | Cook et al. |
| 2012/0078299 | A1 | * | 3/2012 | Ramos Clamote ........... 606/232 |

FOREIGN PATENT DOCUMENTS

| | | |
|---|---|---|
| EP | 0980927 A2 | 2/2000 |
| EP | 0980927 A2 | 2/2000 |
| EP | 1541181 A1 | 6/2005 |

OTHER PUBLICATIONS

Office action received in corresponding European patent application No. 11770281.1-1659 mailed Feb. 6, 2014.

* cited by examiner

TISSUE FIXATOR

CROSS-REFERENCE TO RELATED APPLICATIONS

This application claims priority to U.S. patent application Ser. No. 61/388,056, the disclosure of which is incorporated herein by reference in its entirety.

BACKGROUND

1. Field of Technology

The present disclosure relates generally to tissue graft fixation and, specifically, to components for use in tissue graft fixation.

2. Related Art

In ligament reconstruction surgery, if the graft used is harvested from the quad tendon, the choice to use a particular type of fixation device, namely an Endobutton®, requires the use of a suture and a whip type of stitch, which requires the need to tie a knot. The use of knots involves a certain amount of variation in stiffness from knot to knot. The Endobutton® CL uses a continuous loop of suture, which has no knot and has demonstrated superior strength and stiffness. Methods of fixating an Endobutton® CL to a graft, especially a quad tendon, and devices for use therewith are needed.

SUMMARY

In an aspect, the present disclosure relates to a needle for attaching a fixator to a soft tissue graft. The needle includes a pointed distal end and a proximal end, the proximal end including a suture coupler, the suture coupler including a hook and a pocket formed by the hook, wherein the needle is curved along an entire length of the needle.

In an embodiment, the proximal end further includes a passage and an opening to the passage. In an embodiment, the proximal end further includes a groove on each side of the proximal end. In another embodiment, the needle includes a channel along the length of the needle. In yet another embodiment, the grooves intersect with the pocket. In a further embodiment, the needle further includes a fixator coupled to the needle, the fixator including a flexible member coupled to the fixator, the flexible member coupling the fixator to the needle.

In yet a further embodiment, a portion of the flexible member is housed within the pocket. In an embodiment, portions of the flexible member extending from the pocket are housed within the grooves. In another embodiment, the flexible member is in the form of a continuous loop, the loop including a first end housed within the pocket and a second end coupled to the fixator. In yet another embodiment, the fixator includes at least one hole, the second end of the suture coupled to the fixator via use of the hole. In a further embodiment, the fixator includes two holes, the second end of the suture coupled to the fixator via use of the two holes. In yet a further embodiment, the fixator includes four holes, the second end of the suture couped to the fixator via use of two of the holes, a trailing suture coupled to the third hole, and a leading suture coupled to the fourth hole.

In another aspect, the present disclosure relates to a method of fixating a soft tissue graft to bone. The method including coupling a fixator to the soft tissue graft via use of a needle, the needle including a pointed distal end, and a proximal end, the proximal end including a suture coupler, the suture coupler including a hook and a pocket formed by the hook, wherein the needle is curved along an entire length of the needle; and coupling the soft tissue graft to the bone via use of the fixator.

In an embodiment, the method further includes passing the soft tissue graft through a tunnel within the bone, the bone including a femur. In another embodiment, the fixator includes a flexible member coupled to the fixator, the flexible member coupling the fixator to the needle. In yet another embodiment, a portion of the flexible member is housed within the pocket. In a further embodiment, the flexible member is in the form of a continuous loop, the loop including a first end housed within the pocket and a second end coupled to the fixator.

In yet a further embodiment, the fixator includes at least one hole, the second end of the suture coupled to the fixator via use of the hole. In an embodiment, the fixator includes two holes, the second end of the suture coupled to the fixator via use of the two holes. In another embodiment, the fixator includes four holes, the second end of the suture coupled to the fixator via use of two of the holes, a trailing suture coupled to a third hole, and a leading suture coupled to a fourth hole.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION OF THE EMBODIMENTS

The following description of the preferred embodiment(s) is merely exemplary in nature and is in no way intended to limit the disclosure, its application, or uses.

Figure 1:
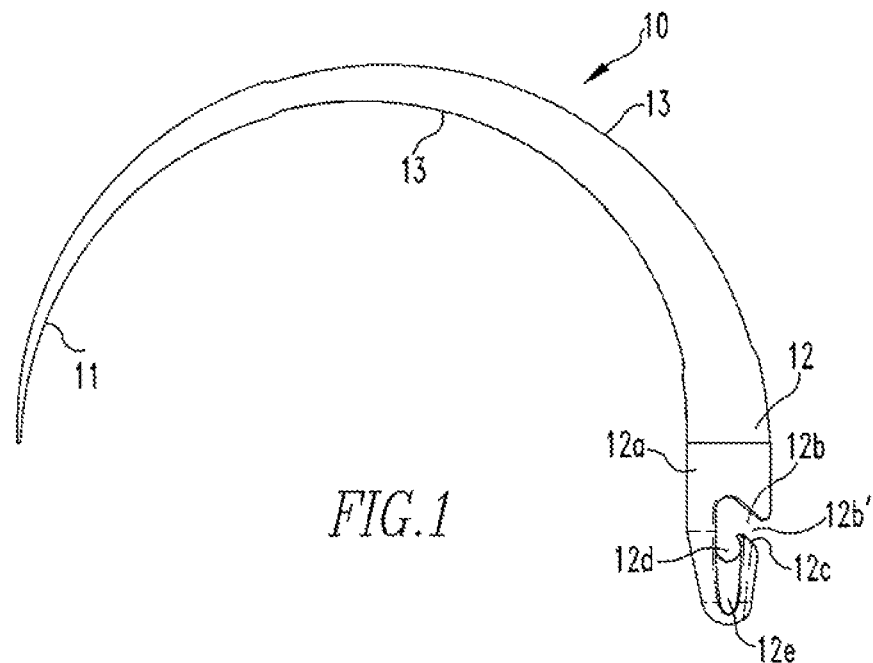
FIG. 1 shows a side view of the needle of the present disclosure.
Figure 2:
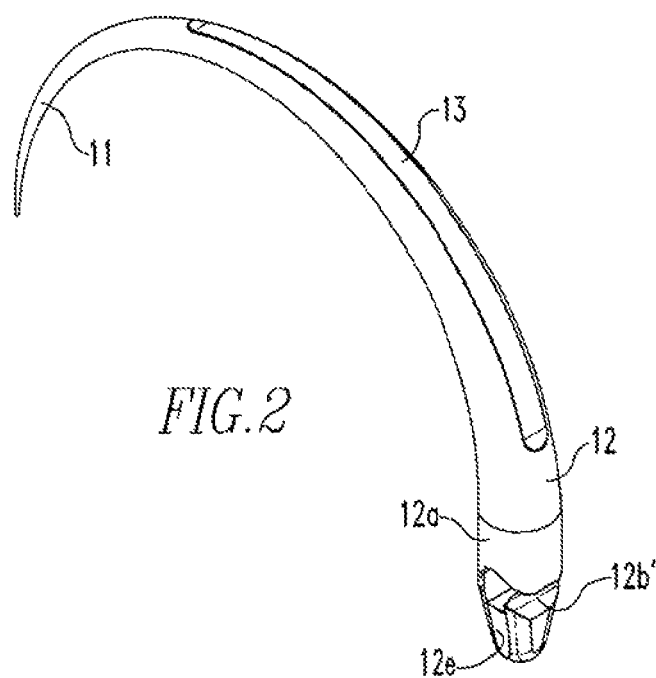
FIG. 2 shows an isometric view of the needle of FIG. 1.

FIGS. 1 and 2 show the needle 10 of the present disclosure. The needle 10 includes a distal end 11 and a proximal end 12. For the purposes of this disclosure, the distal end 11 is pointed. However, it is within the scope of this disclosure for the distal end 11 to not be pointed. The proximal end 12 includes a suture coupler 12a having a passage 12b and an opening 12b' to the passage 12b, a hook 12c, and a pocket 12d formed by the hook 12c. Additionally, the suture coupler 12a includes grooves 12e on each side of the coupler 12a, which intersect with the pocket 12d. For the purposes of this disclosure, the needle 10 is curved along its entire length. However, it is within the scope of this disclosure for the needle 10 to not be curved. Furthermore, the needle 10 includes channels 13 along a length of the needle 10. It is within the scope of this disclosure for the needle to have less than two channels 13 or no channels 13. The purposes of the pocket 12d and the grooves 12e are for housing of a portion or portions of suture, as will be further described below. The needle 10 is made from a biocompatible metal material and via a process known to one of skill in the art. However, other material that would allow the needle 10 to be strong enough to be used for its intended purpose may be used.

Figure 3:
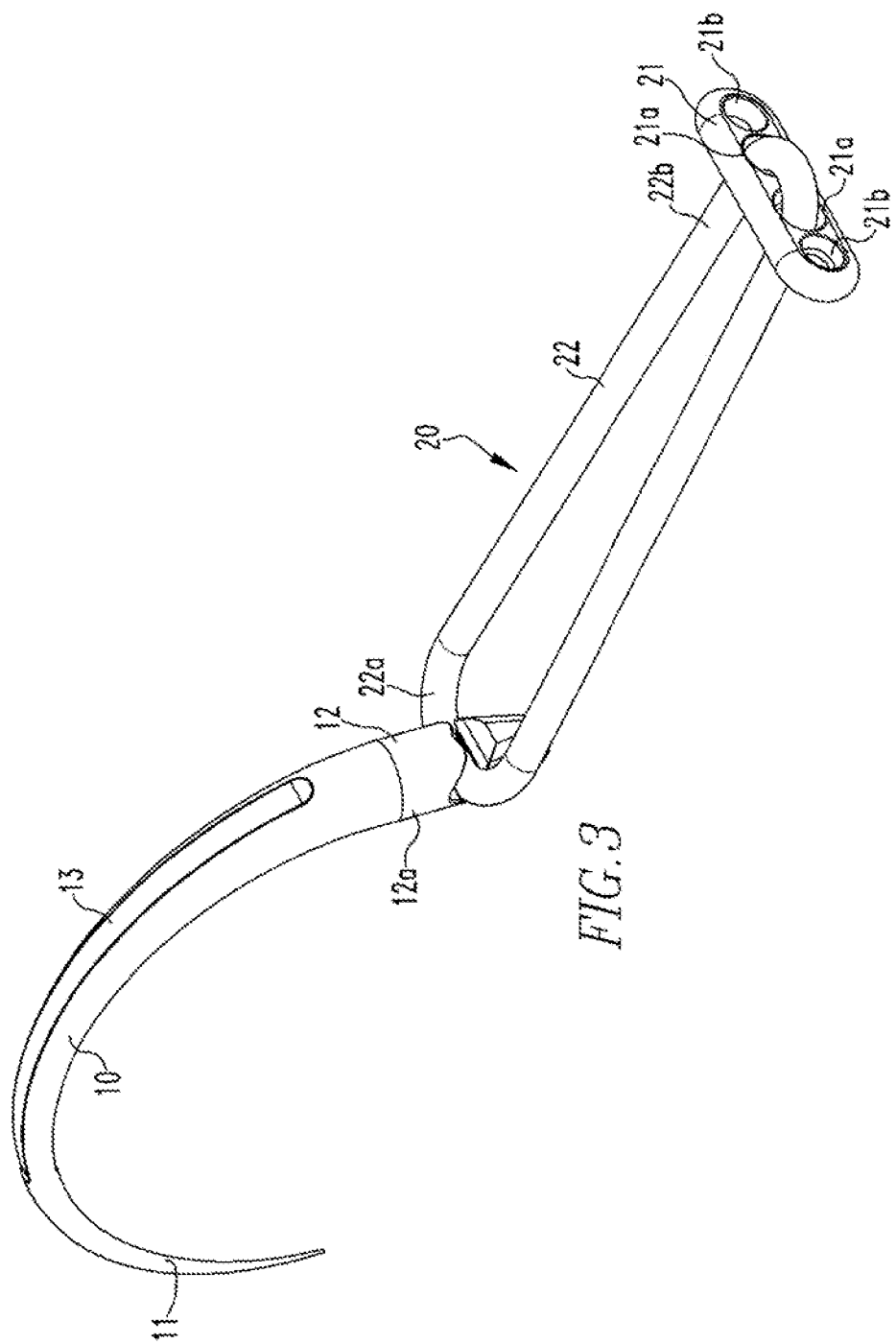
FIG. 3 shows an isometric view of the needle of FIG. 1 coupled to a fixator of the present disclosure.

FIG. 3 shows the needle 10 with a fixator 20 coupled to the needle 10. The fixator 20 is an Endobutton®CL, manufactured and sold by Smith & Nephew, Inc. The fixator 20 includes a fixation device 21 and a closed loop suture 22 coupled to the fixation device 21. A first end 22a of the suture 22 is coupled to the suture coupler 12a by placing the end 22a through the opening 12b' of the passage 12b, through, the passage 12b, and into the pocket 12d. The hook 12c substantially reduces the possibility of the end 22a from escaping the pocket 12d and thereby de-coupling from the needle 10. The fixation device 21 includes four holes 21a, 21b with a second end 22b of the suture 22 coupled to two of the holes 21a. It is within the scope of this disclosure for the fixation device 21 to include one hole 21a and for the end 22a of suture 22 to be coupled to the fixation device 21 via the one hole 21a. Additionally, the fixation device 21 includes two additional holes 21b. These holes 21b are for housing of trailing and leading sutures, as is further described in U.S. Pat. Nos. 5,306,301, 5,645,588, 6,533,802, and 7,530,990, the disclosures of which are incorporated herein by reference in their entireties.

Figure 4:
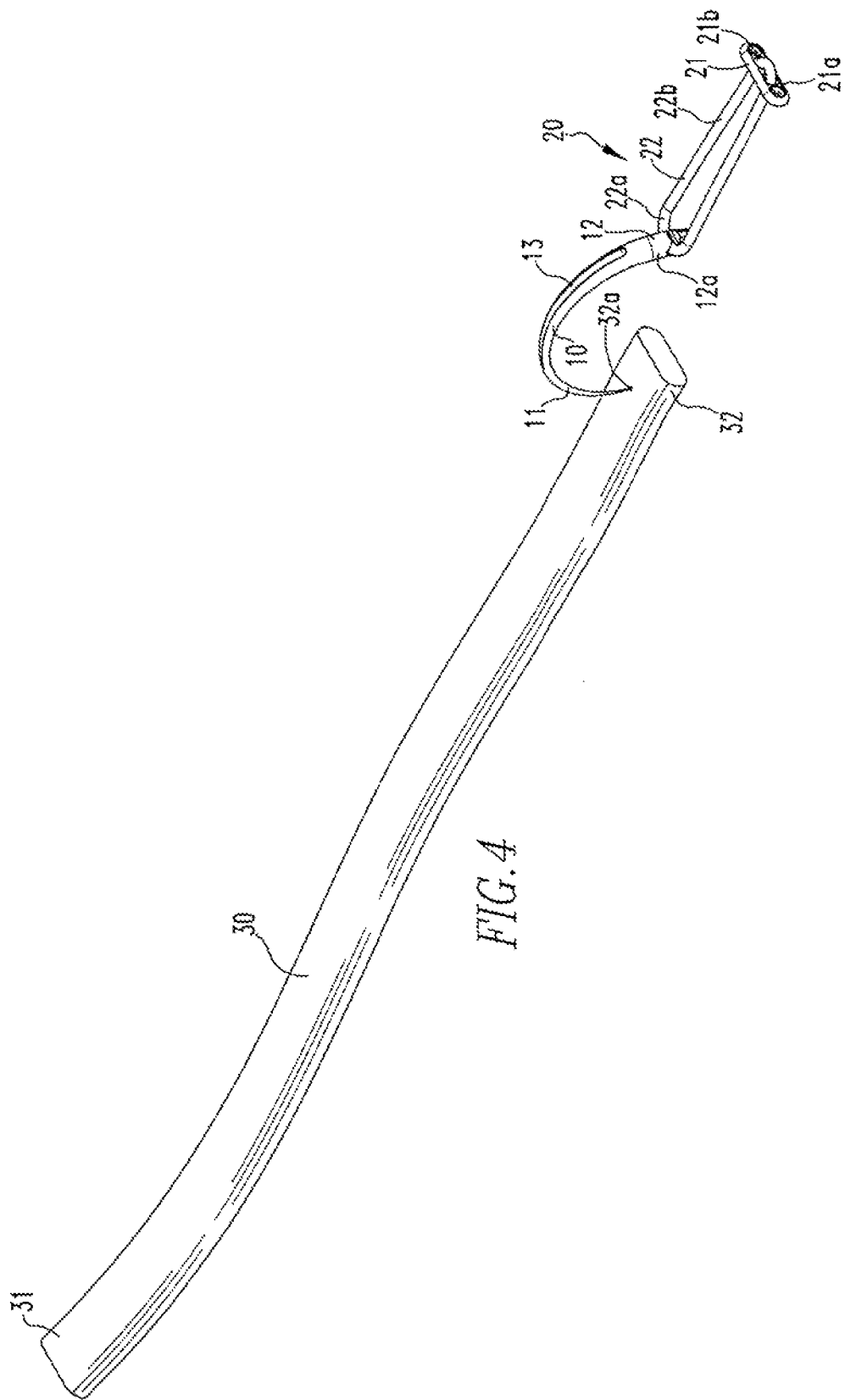
FIGS. 4-12 show the method of fixating a soft tissue graft to bone of the present disclosure.
Figure 5:
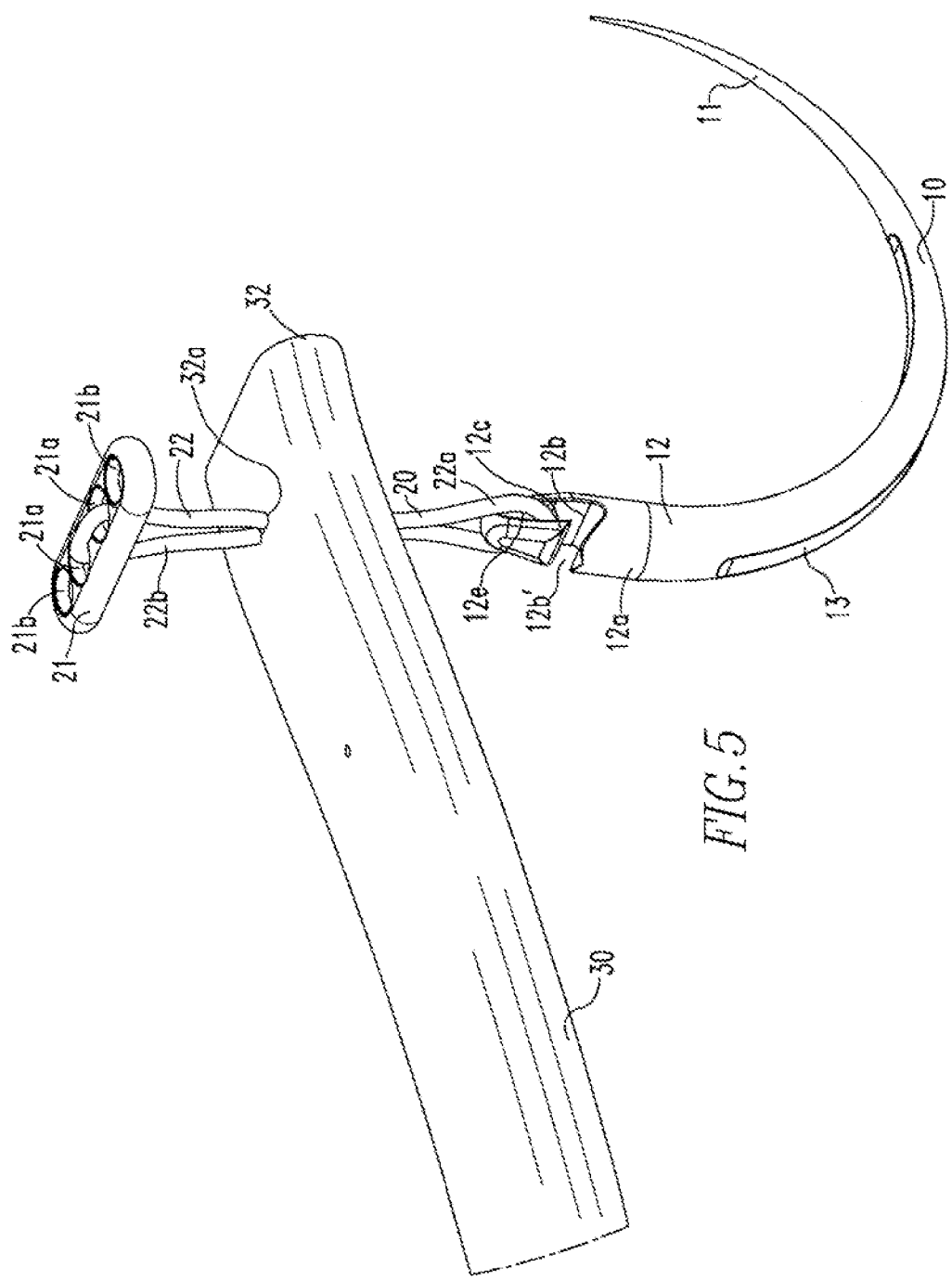
Figure 6:
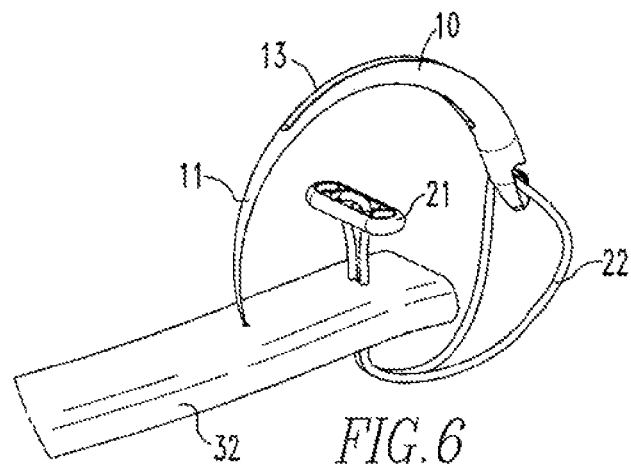
Figure 7:
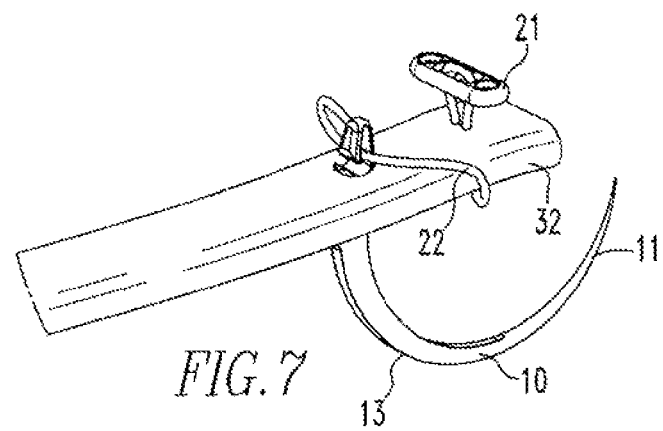
Figure 8:
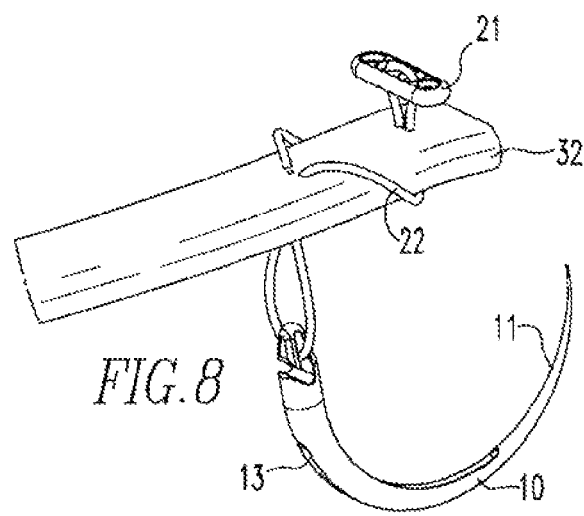
Figure 9:
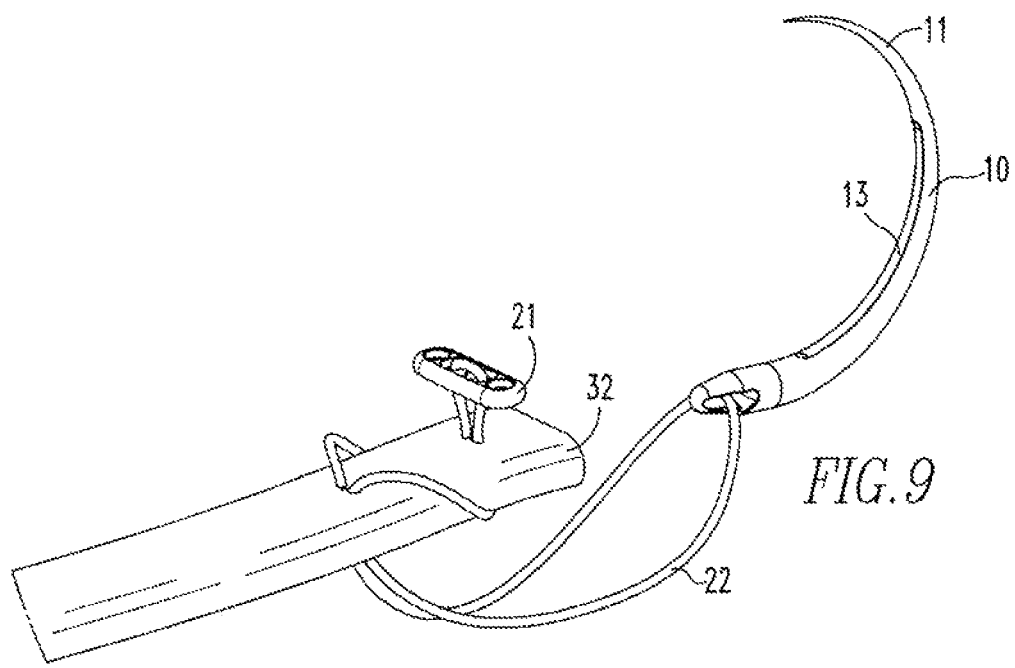
Figure 10:
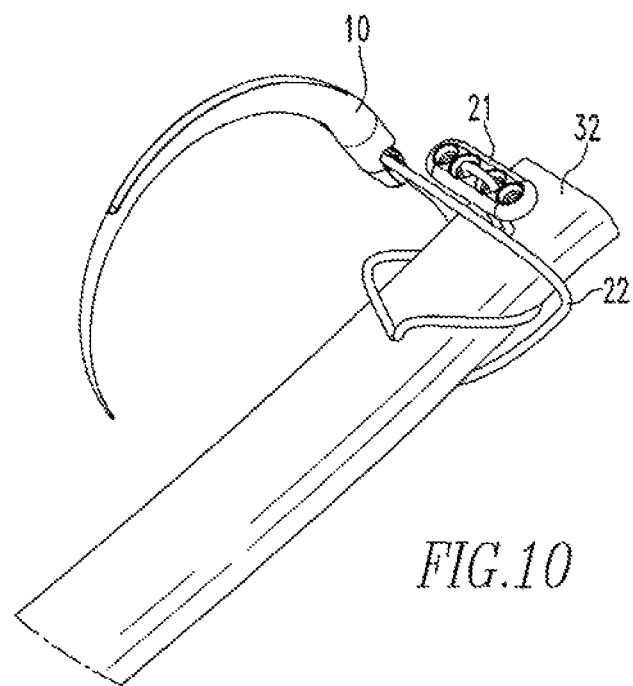
Figure 11:
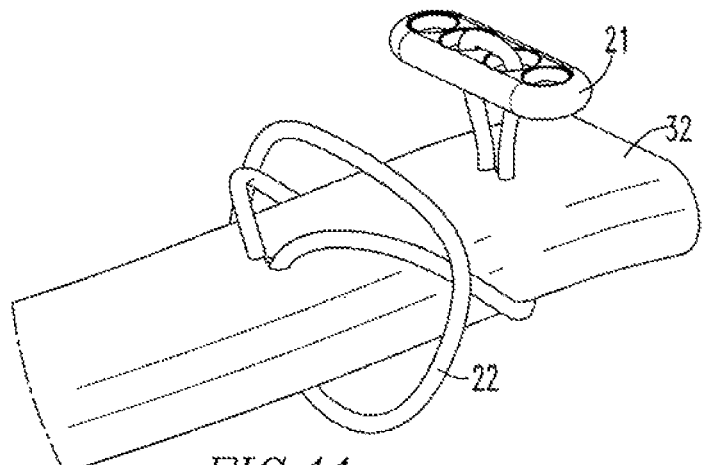
Figure 12:
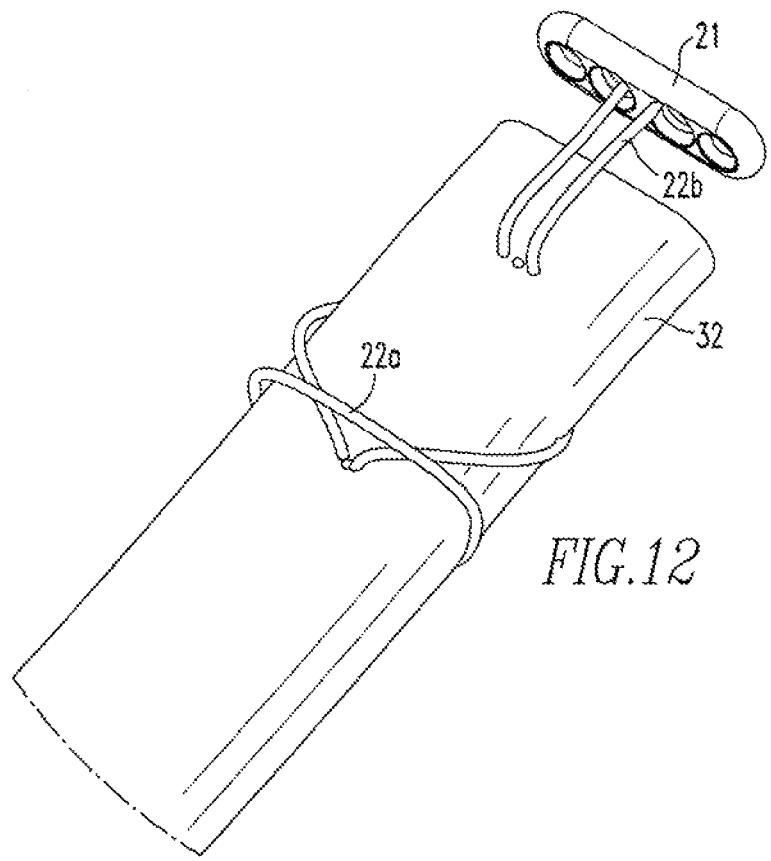

FIGS. 4-12 show a method of coupling a soft tissue graft 30 to bone. FIG. 4 shows a soft tissue graft 30. For the purposes of this disclosure, the graft 30 is a quad tendon. However, the graft 30 could be another human or animal soft tissue or a synthetic tissue. The graft 30 includes a first end 31 and a second end 32. While not shown in FIGS. 4-12, the first end 31 includes bone. The second end 32, which doesn't include bone, is the end that the fixator 20 is coupled to. As shown in FIGS. 4 and 5, the needle 10 is placed through a first location 32a of end 32 and pulled through the graft 30. As shown in FIGS. 6-8, the needle 10 is subsequently brought back around the graft 30, placed through a second location 32b of end 32, and pulled through the graft 30. As shown in FIGS. 9-11, the needle 10 is brought back around the end 32 such that suture end 22a is looped around end 32. The needle 10 may then be removed from the suture 22 by removing needle 10 from end 22a. As shown in FIG. 12, the final step is to pull on the fixation device 21 to tension suture 22 around end 32. For the purposes of this disclosure, the needle 10 is placed through the graft 30 twice. However, it is within the scope of this disclosure to place the needle 10 through the graft 30 more or less than two times.

Once the fixator 20 has been coupled to the graft 30, the graft 30 can be pulled through bone tunnels located in the tibia and femur and the graft 30 may be affixed to the femur by resting the fixation device 21 on the outer surface of the femur, as more fully explained in the '301, '588, '802, and '990 patents. For the purposes of this disclosure, the method involves the use of the needle 10 and fixator 20 with a soft tissue graft in ligament reconstruction surgery on the knee. However, the needle 10 and fixator 20 may be used with a soft tissue graft in connection with another type of surgery.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. An assembly comprising:
a flexible member;
a needle having a pointed distal end, a proximal end of the needle including a hook to which a first end of the flexible member is attached;
a fixation device to which a second end of the flexible member is attached, a lengthwise axis of the fixation device oriented orthogonal with respect to a segment of the flexible member;
wherein the flexible member passes through a hole at a first location of a penetrable element, the penetrable element being synthetic tissue;
wherein the flexible member passes through a hole at a second location of the penetrable element, the hole at the second location disposed further from a distal end of the penetrable element than the hole at the first location;
wherein a first portion of strands of the flexible member is disposed side-by-side, the first portion of strands passing through the hole at the first location of the penetrable element;
wherein a second portion of strands of the flexible member is disposed side-by-side, the second portion of strands passing through the hole at the second location of the penetrable element;
wherein the strands of the flexible member includes a first strand and a second strand;
wherein a portion of the penetrable element resides between a portion of the first strand and the second strand of the flexible member extending between the hole at the first location and the hole at the second location; and
wherein the penetrable element resides between a separation of the strands of the flexible member extending between the hole at the second location of the penetrable element and the first end of the flexible member attached to the proximal end of the needle.

2. The assembly as in claim 1, wherein the needle is curved.

3. The assembly as in claim 2 further comprising:
a trailing suture;
a leading suture;
wherein the hook defines a pocket, an opening to the pocket located on a convex side of the curved needle;
wherein the trailing suture is coupled to the first hole in the fixation device; and
wherein the leading suture is coupled to the second hole in the fixation device.

4. The assembly as in claim 2 further comprising:
a first suture;
a second suture;
wherein the first suture is secured to the first hole in the fixation device; and
wherein the second suture is secured to the second hole in the fixation device.

5. The assembly as in claim 1, wherein the flexible member is a continuous loop of flexible material.

6. The assembly as in claim 1, wherein a first end of the flexible member is attached to the proximal end of the needle; and
wherein a second end of the flexible member is attached to the fixation device.

7. The assembly as in claim 1, wherein the separation of the strands of the flexible member is tensioned around the penetrable element.

8. The assembly as in claim 7, wherein the flexible member is a loop suture.

\* \* \* \* \*